(12) United States Patent
Hoem et al.

(10) Patent No.: US 8,646,325 B2
(45) Date of Patent: Feb. 11, 2014

(54) OPERATING A VESSEL OCCLUSION CATHETER

(75) Inventors: Jon H. Hoem, Oberaegeri (CH); Oliver A. Kohr, Worb (CH)

(73) Assignee: Miracor Medical Systems GmbH, Vienna (AT)

( * ) Notice: Subject to any disclaimer, the term of this patent is extended or adjusted under 35 U.S.C. 154(b) by 675 days.

(21) Appl. No.: 12/786,822

(22) Filed: May 25, 2010

(65) Prior Publication Data

US 2011/0202084 A1 Aug. 18, 2011

(30) Foreign Application Priority Data

Feb. 16, 2010 (EP) ..................................... 10450019

(51) Int. Cl.
*G01F 17/00* (2006.01)

(52) U.S. Cl.
USPC .......................................................... 73/149

(58) Field of Classification Search
USPC .......... 73/149; 604/96.01, 264, 523, 915–920
See application file for complete search history.

(56) References Cited

U.S. PATENT DOCUMENTS

| | | |
|---|---|---|
| 3,275,001 A | 9/1966 | Rosecrans |
| 3,675,658 A | 7/1972 | Taylor |
| 4,589,869 A | 5/1986 | Wernborg |
| 4,657,536 A | 4/1987 | Dorman |
| 4,671,796 A | 6/1987 | Groshong et al. |
| 4,701,166 A | 10/1987 | Groshong et al. |
| 4,705,501 A | 11/1987 | Wigness et al. |
| 4,887,608 A | 12/1989 | Mohl et al. |
| 4,934,996 A | 6/1990 | Mohl et al. |
| 4,943,277 A | 7/1990 | Bolling |
| 4,969,470 A | 11/1990 | Mohl et al. |
| 5,156,600 A | 10/1992 | Young |
| 5,158,529 A | 10/1992 | Kanai |
| 5,201,755 A | 4/1993 | Klement |
| 5,224,938 A | 7/1993 | Fenton, Jr. |
| 5,226,427 A | 7/1993 | Buckberg et al. |
| 5,275,169 A * | 1/1994 | Afromowitz et al. ......... 600/486 |
| 5,466,216 A | 11/1995 | Brown et al. |
| 5,486,192 A | 1/1996 | Walinsky et al. |
| 5,707,358 A | 1/1998 | Wright |
| 5,755,686 A | 5/1998 | O'Neill et al. |
| 5,779,685 A | 7/1998 | Thompson et al. |
| 6,179,815 B1 | 1/2001 | Foote |
| 6,500,145 B1 | 12/2002 | Bicakci et al. |
| 6,506,146 B1 | 1/2003 | Mohl |

(Continued)

FOREIGN PATENT DOCUMENTS

| | | |
|---|---|---|
| UA | 14911 U | 6/2006 |
| WO | WO 8910155 | 11/1989 |

OTHER PUBLICATIONS

European Search Report for Application No. EP 10 45 0019, dated Jun. 25, 2010, 4 pages.

(Continued)

*Primary Examiner* — Peter Macchiarolo
*Assistant Examiner* — Alex Devito
(74) *Attorney, Agent, or Firm* — Fish & Richardson P.C.

(57) ABSTRACT

Some systems and methods for operating a vessel occlusion catheter may include a control and inflation device to control the filling of the balloon in such a manner that the vessel wall will not be overstressed while the safe occlusion of the blood vessel is achieved.

14 Claims, 3 Drawing Sheets

(56) References Cited

U.S. PATENT DOCUMENTS

| | | | |
|---|---|---|---|
| 6,569,145 | B1 | 5/2003 | Shmulewitz et al. |
| 7,331,922 | B2 | 2/2008 | Mohl |
| 2002/0120232 | A1 | 8/2002 | Stumpp et al. |
| 2008/0015404 | A1 | 1/2008 | Mohl |
| 2008/0119742 | A1 | 5/2008 | Mohl |
| 2010/0056849 | A1 | 3/2010 | Mohl |
| 2010/0130810 | A1 | 5/2010 | Mohl |
| 2013/0090678 | A1 | 4/2013 | Hoem et al. |
| 2013/0090679 | A1 | 4/2013 | Hoem et al. |

OTHER PUBLICATIONS

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010]. Retrieved from the Internet: <URL: http://www.anesthesia-analgesia.org/content/97/1/298.full.pdf>.

'Global Myocardial Protection' [online] Edwards Lifesciences, 2004 [retrieved May 27, 2010]. Retrieved from the Internet: <URL: htip://ht.edwards.com/resourcegallery/products/cannulae/images/ar00519.pdf>.

'Myocardial Protection System' [online] Quest Medical, Inc. 2010 [retrieved May 27, 2010]. Retrieved from the Internet: <URL: http://www.questmedical.com/products/mps.asp>.

'Cardioplegia Delivery' [online] Quest Medical, Inc. 2010 [retrieved May 27, 2010]. Retrieved from the Internet: <URL: http://www.questmedical.com/products/cardio_catheters.asp>.

'Cannulation' [online] Medtronic, Inc. 2010 [retrieved May 27, 2010]. Retrieved from the Internet: <URL: http://www.medtronic.com/for-healthcare-professionals/products-therapies/cardiovascular/therapies/cannulation/index.htm>.

'MiRCSP Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/mircsp-cannula/index.htm>.

'Retrograde Perfusion Cannulae' [online]. Medtronic, Inc. 2010 [retrieved May 27, 2010]. Retrieved from the Internet: <URL: http://www:medtronic.com/for-healthcare-professionals/products-therapies/cardiovascular/cannulae-products/retrograde-perfusion-cannulae/index.htm>.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>.

Mohl, Werner et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Mohl, Werner et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.

Mohl, Werner et al. "Coronary Sinus Library, ICSO and PICSO" Society of Coronary Sinus Interventions, 2003. A. Holzhausens Nfg., Austria.

Mohl et al., "Intermittent pressure elevation of the coronary venous system as a method to protect ischemic myocardium," *Interact CardioVac Thorac Surg.*, 2005, 4:66-69.

Syeda et al., "The salvage potential of coronary sinus interventions: Meta-analysis and pathophysiologic consequences," *J Thorac Cardiovasc Surg.*, 2004, 124:1703-1712.

\* cited by examiner

OPERATING A VESSEL OCCLUSION CATHETER

CROSS-REFERENCES TO RELATED APPLICATION(S)

This application claims priority to European Patent Application No. 10 450 019.4 filed on Feb. 16, 2010, the content of which is incorporated herein by reference.

TECHNICAL FIELD

This document relates to systems and methods for inflating and deflating a balloon of a vessel occlusion catheter device arranged in a body vessel.

BACKGROUND

Balloon catheters have been used for a number of medical applications. A balloon catheter comprises a balloon which can be brought from the deflated state into the expanded state by the introduction of a fluid, and from the expanded state back into the deflated state by evacuation. The fluid may be comprised of a gas or a liquid.

Balloon catheters are, for instance, used for the balloon dilatation of constricted blood vessels in the context of a percutaneous transluminal angioplasty. In that case, a balloon attached to a vascular catheter is advanced within a blood vessel as far a to a pathologically constricted vascular site, and the balloon is deployed on the constricted site under a high pressure (6 to 20 bar). This causes the constrictions, which are primarily due to arteriosclerotic vascular sclerosis, to be dilated until they will no longer, or less strongly, impair the blood flow.

Balloon catheters may, however, also be employed in the context of a pressure-controlled intermittent occlusion of a body vessel and, in particular, the coronary sinus. Methods for the pressure-controlled intermittent occlusion of the coronary sinus are, for instance, described in the documents EP 609914 A1, EP 230996 A2, EP 1406683 A2, EP 1753483 A1, EP 1755702 A1 and WO 2008/064387 A1. In those methods, the coronary sinus is cyclically occluded and released again by using a balloon, the occlusion of the coronary sinus, during the occlusion phases, inducing a pressure increase and hence a retroperfusion of blood via the respective vein into the nutritive capillaries of the ischemic region so as to enable a redistribution of flow into those regions. Upon release of the occlusion, the retroperfused blood is flushed out while metabolic waste products are, at the same time, discharged. The pressure in the occluded coronary sinus is each measured during the occlusion phases, the release of the occlusion as well as the initiation of the occlusion occurring as a function of the measured pressure values.

As opposed to a balloon dilatation in the context of a percutaneous transluminal angioplasty, the pressure-controlled intermittent occlusion of a blood vessel and, in particular, the coronary sinus does not aim to inflate the balloon with such a high pressure as to cause an irreversible deformation and, in particular, expansion of the respective vascular region. The inflation of the balloon rather is to be controlled in a manner that the balloon exerts a pressure on the vessel wall, which will just do to occlude the blood vessel to a sufficiently safe extent and prevent blood from flowing past the balloon. If too high a pressure is fed to the balloon, this will cause too strong a radial expansion of the blood vessel, whereby the respective mechanical load on the vessel wall may lead to irreversible damage, which is to be prevented anyhow. On the other hand, too small a pressure supply to the balloon would save the vessel wall, yet the balloon would not completely occlude the vessel.

SUMMARY

Some embodiments of a system or method for controlling the inflation of a balloon catheter arranged in a blood vessel can provide a process by which it is feasible to control the filling of the balloon in such a manner that the vessel wall will not be overstressed while safely occluding of the blood vessel.

In particular embodiments, some systems and methods for operating a vessel occlusion catheter may include a control and inflation device to control the filling of the balloon in such a manner that the vessel wall will not be irreversible deformed while the safe occlusion of the blood vessel is achieved. For example, a coronary sinus occlusion catheter may include a balloon device that is repeatedly inflated and deflated to intermittently occlude the coronary sinus. A control system for the occlusion catheter can include the control and inflation device having components to inflate and deflate the balloon device in a safe manner that reduces the likelihood of overstressing the vessel wall of the coronary sinus.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
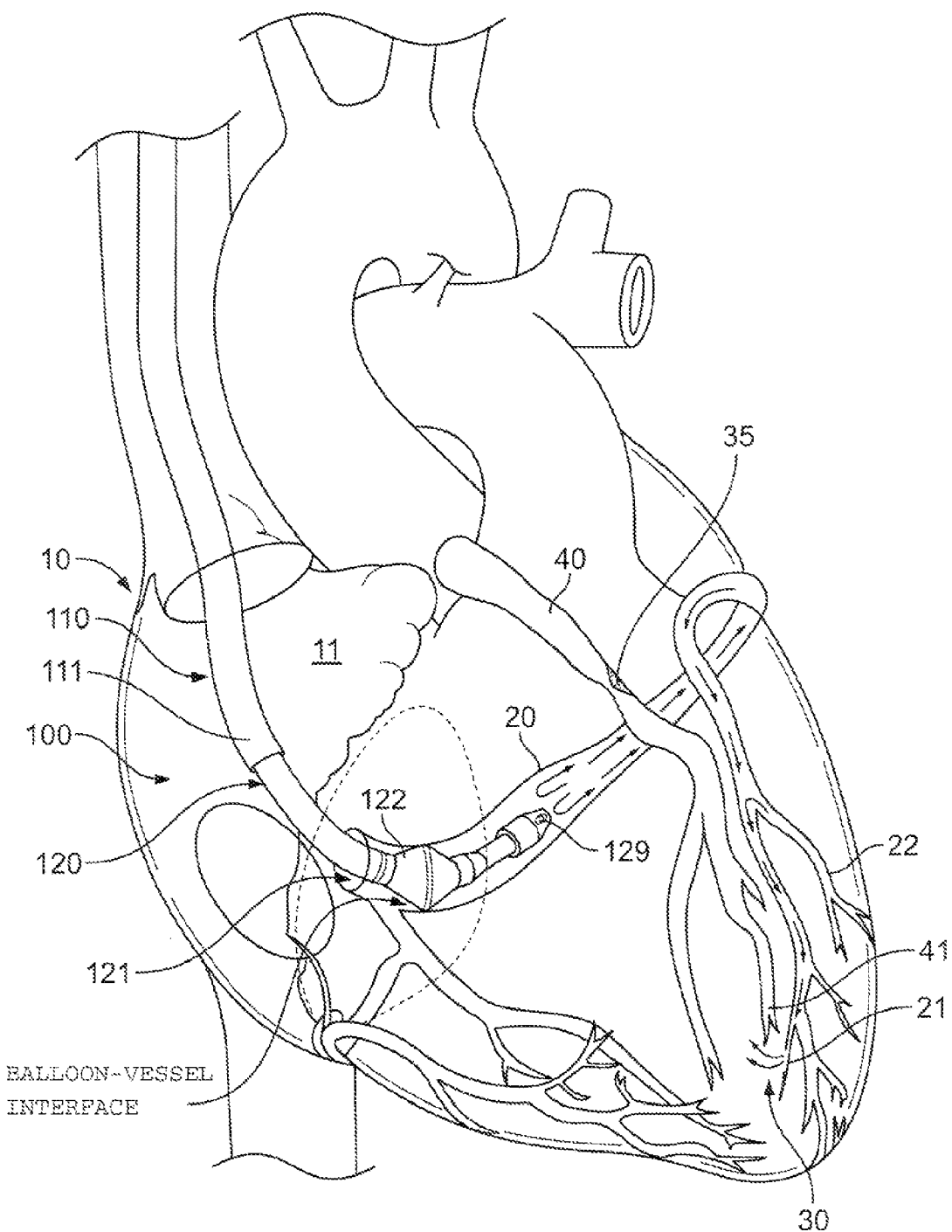
FIG. 1 is a perspective view of a portion of a system for treating heart tissue, in accordance with some embodiments.
Figure 2:
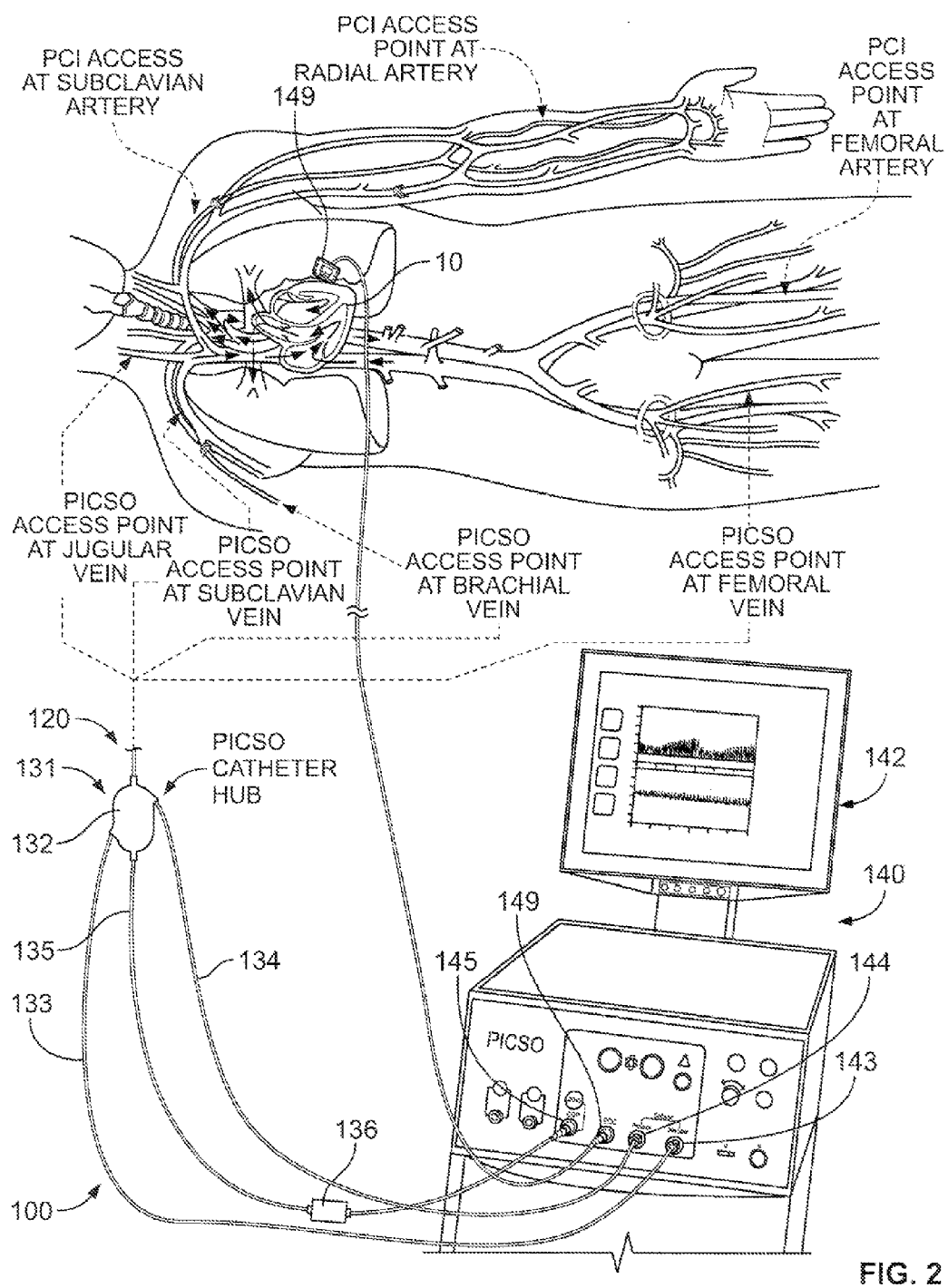
FIG. 2 is a perspective view of another portion of the system of FIG. 1.

Referring to FIGS. 1-2, some embodiments of a system 100 for treating heart tissue can include a coronary sinus occlusion catheter 120 and a control system 140 (FIG. 2). In particular embodiments, the control system 140 can be configured to control the operation of the catheter 120 for providing pressure-controlled intermittent coronary sinus occlusion (PICSO) and to receive heart sensor data for display. The coronary sinus occlusion catheter 120 includes a distal tip portion 121 (leading to a distal end depicted in FIG. 1) and a proximal portion 131, which includes a proximal hub 132 that is coupled to the control system 140 via a number of fluid or sensor lines 133, 134, and 135. Accordingly, the control system 140 may be employed to operate one or more components at the distal tip portion 121 of the coronary sinus occlusion catheter 120 while also receiving one or more sensor signals that provide data indicative of heart characteristics (e.g., coronary sinus pressure, electrocardiogram (ECG) information, and the like).

Briefly, in use, the distal tip portion 121 of the coronary sinus occlusion catheter 120 can be arranged in a coronary sinus 20 of a heart 10 and thereafter activated to intermittently occlude the blood flow exiting from the coronary sinus 20 and into the right atrium 11. During such an occlusion of the coronary sinus 20, the venous blood flow that is normally exiting from the coronary sinus 20 may be redistributed into a portion of heart muscle tissue 30 that has been damaged due to blood deprivation. For example, the portion of heart muscle tissue 30 can suffer from a lack of blood flow due to a blockage 35 in a coronary artery 40. As a result, the arterial blood flow to the affected heart muscle tissue 30 via a local artery 41 can be substantially reduced such that the heart muscle tissue 30 becomes ischemic or otherwise damaged. Further, because the arterial blood flow is reduced, the venous blood flow exiting from the local vein 21 is likewise reduced. Other branch veins 22 located at different regions along the heart 10 may continue to receive blood flow, thereby creating a supply of venous blood flow exiting through the coronary sinus 20. In some embodiments, the coronary sinus occlusion catheter 120 can be delivered into the coronary sinus 20 and thereafter activated so as to intermittently occlude the coronary sinus 20 before, during, or after treating the blockage 35 on the arterial side. Such an occlusion can cause the venous blood flow to be redistributed to the local vein 21 and then into the portion of heart muscle tissue 30 can suffer from a lack of blood flow due to a blockage 35 in a coronary artery 40. As such, the ischemic or otherwise damaged heart muscle tissue 30 can be treated (e.g., reduction of border zone infarct size) with the redistributed venous blood flow in that the heart muscle tissue 30 receives an improved redistribution of flow before, during, and after the blockage 35 is repaired or removed to restore normal coronary arterial blood flow.

Furthermore, in use, the control system 140 (FIG. 2) is configured to provide automated control of an occlusion component (e.g., an inflatable balloon 122 or the like) of the coronary sinus occlusion catheter 120. As described in more detail below, the control system 140 includes a computer processor that executes computer-readable instructions stored on a computer memory device so as to activate or deactivate the occlusion in the coronary sinus 20 in accordance with particular patterns. For instance, the control system 140 can be configured to activate the occlusion component of the catheter 120 in the coronary sinus 20 as part of a predetermined pattern of occlusion periods and release periods that is independent of the coronary sinus pressure, or as part of a pressure-dependent pattern that is at least partially defined by the coronary sinus pressure readings during the procedure. In addition, the control system 120 is equipped with a display device 142 having a graphical user interface that provides a cardiologist or other user with time-sensitive, relevant data indicative of the progress of a coronary sinus occlusion procedure and the condition of the heart 10. As such, the user can readily monitor the patient's condition and the effects of intermittently occluding the coronary sinus 20 by viewing the graphical user interface while contemporaneously handling the coronary sinus occlusion catheter 120 other heart treatment instruments (e.g., angioplasty catheters, stent delivery instruments, or the like). It should be understood from the description herein that, in some embodiments, the control system 140 and the coronary sinus occlusion catheter 120 can be used as part of a system for treating the heart muscle tissue before, during, and after the blockage 35 is repaired or removed to restore normal coronary arterial blood flow.

Referring in more detail to FIG. 1, the coronary sinus occlusion catheter 120 can be delivered via the venous system to the coronary sinus 20 before, during, or after repairing or treating the blockage 35 the coronary artery 40. In such circumstances, the portion of heart muscle tissue 30 that is damaged due to lack of arterial blood flow (as a result of the blockage) can be treated with a supply of venous blood while the normal arterial blood flow is restored (as a result of repairing or removing the blockage 35).

The system 100 may include a guide member 110 that is advanced through the venous system of the patient and into the right atrium 11. The guide member 110 in this embodiment comprises a guide sheath having a lumen extending between a distal end 111 (FIG. 1) and a proximal end (not shown). In alternative embodiments, the guide member 110 can include a guide wire having an exterior surface extending between the distal end and the proximal end. Optionally, the guide member 110 includes a steerable mechanism to control the orientation of the distal end so as to steer the distal end 111 through the venous system and into the right atrium 11. Also, the guide member 110 can include one or more marker bands along the distal end 111 so that the position of the distal end can be monitored during advancement using an imaging device.

After the guide member 110 is advanced into the right atrium 11, the distal end 111 may be temporarily positioned in the coronary sinus 20. From there, the distal tip portion 121 of the coronary sinus occlusion catheter 120 can be slidably advanced along the guide member 110 for positioning inside the coronary sinus 20. In the embodiments in which the guide member 110 comprises a guide sheath, the distal tip portion 121 of the coronary sinus occlusion catheter 120 can slidably engage with an interior surface of the lumen during advancement toward the coronary sinus 20. In the alternative embodiments in which the guide member 110 comprises a guide wire structure, the distal tip portion 121 of the coronary sinus occlusion catheter 120 can slidably advance over the exterior surface of the guide wire (e.g., a lumen of the catheter 120 passes over the guide wire) during advancement toward the coronary sinus 20. After the coronary sinus occlusion catheter 120 reaches the coronary sinus 20, the distal end 111 of the guide member 110 can be withdrawn from the coronary sinus 20 and remain in the right atrium 11 during use of the coronary sinus occlusion catheter 120.

Still referring to FIG. 1, the distal tip portion 121 of the coronary sinus occlusion catheter 120 that is positioned in the coronary sinus 20 includes an occlusion component 122, which in this embodiment is in the form of an inflatable balloon device. The occlusion component 122 can be activated so as to occlude the coronary sinus 20 and thereby cause redistribution of the venous blood into the heart muscle tissue 30 that is damaged due to a lack of arterial blood flow. As described in more detail below, the inflatable balloon device 122 can be in fluid communication with an internal lumen of the coronary sinus occlusion catheter 120, which is in turn in communication with a pneumatic subsystem of the control system 140 (FIG. 2). As such, the control system 140 can be employed to expand or deflate the balloon device 122 in the coronary sinus.

The distal tip portion 121 also includes a one or more distal ports 129 that are positioned distally forward of the inflatable balloon device. In the depicted embodiments, the distal ports 129 face is a generally radially outward direction and are substantially uniformly spaced apart from one another along the circumference of the distal tip. As described in more detail below, the distal ports 129 may all be in fluid communication with a single pressure sensor lumen extending through the coronary sinus occlusion catheter 120. Accordingly, the coronary sinus pressure can be monitored via a pressure sensor device that is in fluid communication with the distal ports 129.

Referring now to FIG. 2, the proximal portion 131 of the coronary sinus occlusion catheter 120 and the control system 140 are positioned external to the patient while the distal tip portion 121 is advanced into the coronary sinus 20. The proximal portion 131 includes the proximal hub 132 that is coupled to the control system 140 via a set of fluid or sensor lines 133, 134, and 135. As such, the control system 140 can activate or deactivate the occlusion component 122 at the distal tip portion 121 of the coronary sinus occlusion catheter 120 while also receiving one or more sensor signals that provide data indicative of heart characteristics (e.g., coronary sinus pressure, electrocardiogram (ECG) information, and the like).

The proximal hub 132 of the coronary sinus occlusion catheter 120 serves to connect the plurality of fluid or sensor lines 133, 134, and 135 with the portion of the coronary sinus occlusion catheter 120 that extends into the patient's venous system. For example, the first line 133 extending between the control system 140 and the proximal hub 132 comprises a fluid line through which pressurized fluid (e.g., helium, another gas, or a stable liquid) can be delivered to activate the occlusion component (e.g., to inflate the inflatable balloon device 122). The fluid line 133 is connected to a corresponding port 143 of the control system 140 (e.g., the drive lumen port in this embodiment) so that the line 133 is in fluid communication with the control and inflation device 200 (refer to FIG. 3) at least partially housed in the control system 140. The proximal hub 132 joins the first line 133 with a balloon control lumen extending through the coronary sinus occlusion catheter 120 and to the inflatable balloon device 122.

In another example, the second line 134 extending between the control system 140 and the proximal hub 132 comprises a balloon sensor line that is in fluid communication with the interior of the inflatable balloon device 122 so as to measure the fluid pressure within the balloon device 122. The proximal hub 132 joins the second line 134 with a balloon pressure lumen extending through the coronary sinus occlusion catheter 120 and to the inflatable balloon device 122. The pressure of the balloon device 122 may be monitored by a component of the control and inflation device 200 (refer to FIG. 3) at least partially housed in the control system 140. The balloon sensor line 134 is connected to a corresponding port 144 of the control system 140 so that a pressure sensor arranged within the control system 140 can detect the fluid pressure in the balloon device 122. Alternatively, the pressure sensor may be arranged in the distal tip portion 121 or the in the proximal hub 132 such that only a sensor wire connects to the corresponding port 144 of the control system 140.

The proximal hub also connects with a third line 135 extending from the control system 140. The third line 135 comprises a coronary sinus pressure line that is used to measure the fluid pressure in the coronary sinus both when the balloon device 122 is inflated and when it is deflated. The proximal hub 132 joins the third line 135 with a coronary sinus pressure lumen extending through the coronary sinus occlusion catheter 120 and to the distal ports 129 that are forward of the balloon device 122. As such, the coronary sinus pressure lumen 125 and at least a portion of the third line 135 may operate as fluid-filled path (e.g., saline or another biocompatible liquid) that transfers the blood pressure in the coronary sinus 20 to pressure sensor device 136 along a proximal portion of the third line 135. The pressure sensor device 136 samples the pressure measurements (which are indicative of the coronary sinus pressure) and outputs an sensor signal indicative of the coronary sinus pressure to the corresponding port 145 of the control system 140 for input to an internal control circuit (which may include one or more processors that execute instructions stored on one or more computer memory devices housed in the control system 140). As described in more detail below, the coronary sinus pressure data are displayed by the graphical user interface 142 in a graph form so that a cardiologist or other user can readily monitor the trend of the coronary sinus pressure while the coronary sinus 20 is in an occluded condition and in an non-occluded condition. Optionally, the graphical user interface 142 of the control system 140 can also output a numeric pressure measurement on the screen so that the cardiologist can readily view a maximum coronary sinus pressure, a minimum coronary sinus pressure, or both. In alternative embodiments, the pressure sensor device 136 can be integrated into the housing of the control system 140 so that the third line 135 is a fluid-filled path leading up to the corresponding port 145, where the internal pressure sensor device (much like the device 136) samples the pressure measurements and outputs a signal indicative of the coronary sinus pressure.

Still referring to FIG. 2, the system 100 may include one or more ECG sensors 149 to output ECG signals to the control system 140. In this embodiment, the system 100 includes a pair of ECG sensor pads 149 that are adhered to the patient's skin proximate to the heart 10. The ECG sensors 149 are connected to the control system 140 via a cable that mates with a corresponding port 149 along the housing of the control system 140. As described in more detail below, the ECG data can be displayed by the graphical user interface 142 in a graph form so that a cardiologist or other user can readily monitor the patient's heart rate and other characteristics while the coronary sinus is in an occluded condition and in an non-occluded condition. Optionally, the graphical user interface 142 of the control system 140 can also output numeric heart rate data (based on the ECG sensor data on the screen so that the cardiologist can readily view the heart rate (e.g., in a unit of beats per minutes). The ECG sensor signals that are received by the control system 140 are also employed by the internal control circuit so as to properly time the start of the occlusion period (e.g., the start time at which the balloon device 122 is inflated) and the start of the non-occlusion period (e.g., the start time at which the balloon device 122 is deflated).

As shown in FIG. 2, the coronary sinus occlusion catheter 120 is delivered to the heart 10 via a venous system using any one of a number of venous access points. Such access points may be referred to as PICSO access points in some embodiments in which the coronary sinus occlusion catheter 120 is controlled to perform a PICSO procedure for at least a portion of the time in which the catheter 120 is positioned in the coronary sinus 20. For example, the guide member 110 and the distal tip portion 121 can be inserted into the venous system into an access point at a brachial vein, an access point at a subclavian vein, or at an access point at a jugular vein. From any of these access points, the guide member 110 can be advanced through the superior vena cava and into the right atrium 11. Preferably, the guide member 110 is steered into an ostial portion of the coronary sinus 20, and then the distal tip portion 121 of the catheter 120 is slidably advanced along the guide member 110 and into the coronary sinus 20 before the guide member 110 is backed out to remain in the right atrium 11. In another example, the guide member 110 and the distal tip portion 121 can be inserted into the venous system into an access point at a femoral vein. In this example, the guide member 110 can be advanced through the inferior vena cava and into the right atrium 11. As previously described, the distal tip portion 121 of the catheter 120 is slidably advanced along the guide member 110 and into the coronary sinus 20 before the guide member 110 is backed out to remain in the right atrium 11.

In some embodiments, the blockage 35 in the heart may be repaired or removed using a percutaneous coronary intervention (PCI) instrument such as an angioplasty balloon catheter, a stent delivery instrument, or the like. The PCI instrument may access the arterial system via any one of a number of PCI access points, as shown in FIG. 2. In some implementations, the PCI instrument can be inserted into the arterial system into an access point at a femoral artery, an access point at a radial artery, or an access point at a subclavian artery. Thus, as previously described, some embodiments of the system 100 may employ a PICSO access point into the venous system while a PCI access point is employed to insert a PCI instrument into the arterial system.

Figure 3:
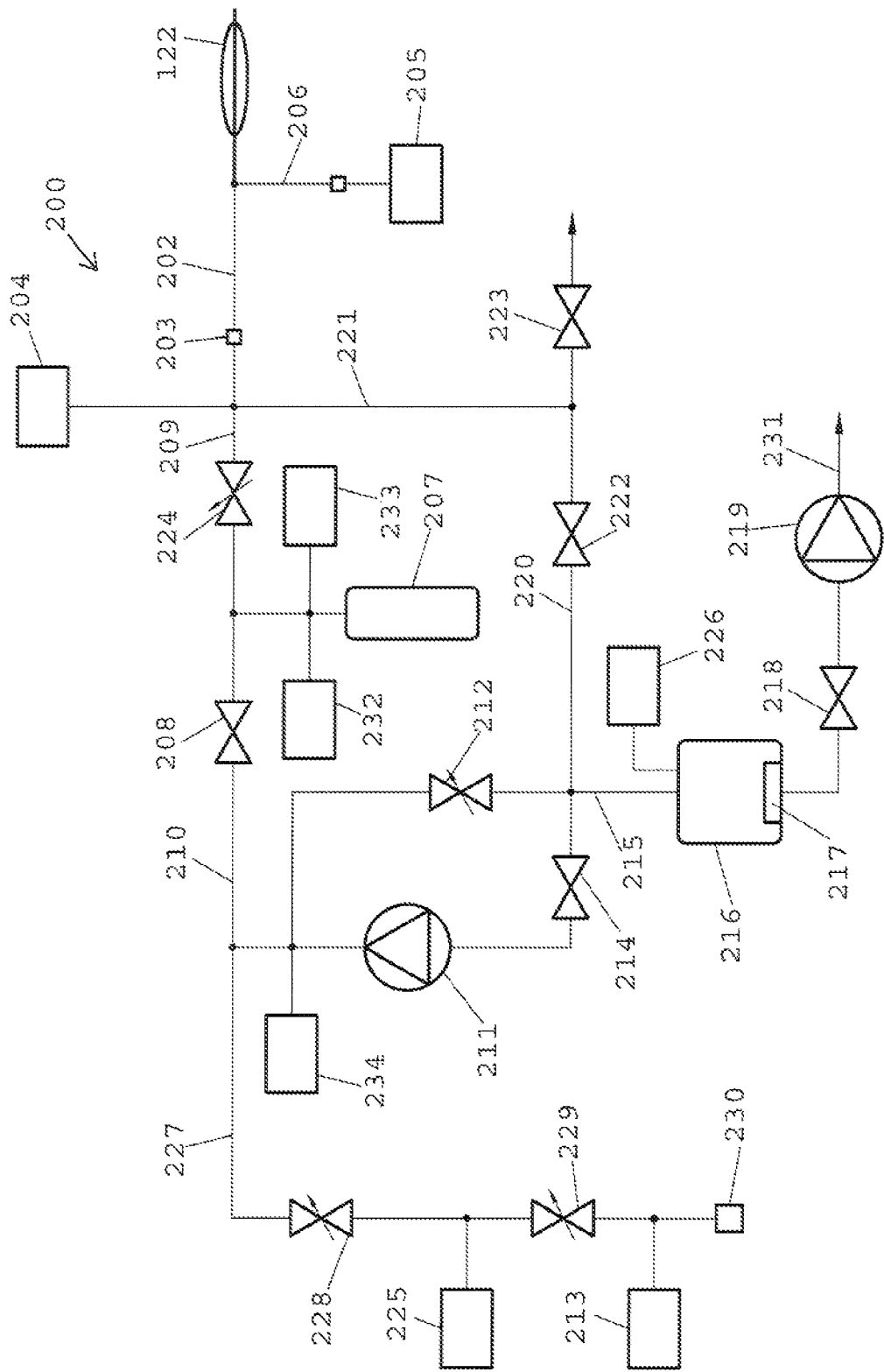
FIG. 3 is a block diagram of a control and inflation device of the system of FIG. 2.

Referring now to FIG. 3, some embodiments of the control system 140 include the control and inflation device 200 having components to inflate and deflate the balloon device 122 of the catheter 120. As previously described, the control system may further include one or more processors (not shown in FIG. 3) that are configured to execute various software modules stored on at least one memory device (not shown in FIG. 3). In some embodiments, a balloon inflate and deflate software module can be stored on the memory device to provide computer-readable instructions that, when executed by one of the processors (such as an embedded microprocessor), causes the control and inflation device 200 to inflate or deflate the balloon device 122 at selected times. In some embodiments, the balloon inflate and deflate software module stored on the memory device can implement a customized algorithm that calculates and updates the time periods during which the coronary sinus is in an occluded state and in a non-occluded state based upon the coronary sinus pressure measurements. In such circumstances, the coronary sinus 20 is not occluded and non-occluded according to a predetermined pattern of inflated times and deflated times that are independent of the patient, but instead the coronary sinus pressure measurements at least partially dictate the time periods during which the coronary sinus is in an occluded state and in a non-occluded state. In alternative modes, the balloon inflate and deflate software module stored on the memory device may cause the coronary sinus 20 to be occluded and non-occluded according to a predetermined pattern of inflated times and deflated times that are independent of the patient and the coronary sinus pressure measurements. The processors of the control system 140 may include, for example, microprocessors that are arranged on a motherboard so as to execute the control instructions of the control system 140. The memory device of the control system 140 may include, for example, a computer hard drive device having one or more discs, a RAM memory device, that stored the various software modules.

As shown in FIG. 3, the control and inflation device 200 can be configured to promptly inflate or deflate the balloon device 122. The balloon device 122 is connected to the connection 203 of the control and inflation device via an inflation lumen 202. The pressure in the inflation lumen 202 can be measured via a schematically illustrated pressure measuring device 204. A further measurement for the balloon pressure can be obtained via a further pressure measuring device 205. The pressure measuring device 205 is connected with the balloon 122 via a separate pressure measuring lumen 206.

The control and inflation device comprises a pressure tank 207, which can be connected via the control valves 208 or 224 either with the connection 203 via line 209 or with the fluid loop via line 210. Pressure measuring devices for measuring the pressure prevailing in the pressure tank 207 are designated by reference numbers 232 and 233. Furthermore, a pump 211 is provided in parallel with a stop valve 212 (and, optionally, a throttle valve). A conductive connection between the pump 211 and the vacuum tank 216 can be established via a stop valve 214 and a line 215. The condensate possibly collecting in the vacuum tank 216 is schematically indicated at 217 and can be pumped off via a stop valve 218 by the aid of the condensate pump 219. Connection lines 220 and 221 can be brought into a conductive connection with the vacuum tank 216 via a stop valve 222. In order to determine the pressure prevailing in the vacuum tank 216 a pressure measuring device 226 is provided.

An emergency valve is denoted by 223.

The feed-in for the fluid loop takes place via line 227, to which a fluid reservoir 230, e.g. a helium cylinder, may be connected via a throttle valve 228 and a stop valve 229.

In the following, the mode of functioning of the control and inflation device will be explained in more detail.

Set-Up Mode:

In the set-up mode, all components of the system are initially filled with air or the like, and the valves are closed.

Evacuation:

In the evacuation mode, the whole system is evacuated. To this end, the stop valves 223 and 229 are closed, whereas all other valves are open. The air possibly present in the system is evacuated by the aid of the condensate pump 219, the air possibly present in the system escaping along arrow 231. The balloon 122 is also evacuated and deflated.

In the evacuated state a leak-tightness test can be conducted. In particular the leak-tightness of the control and inflation device, the balloon and the catheter as well as possible further volumes connected thereto can be checked, whereby the components can be regarded as tight if the evacuated state is maintained over a predetermined period of time.

System Filling:

The system is then filled with a fluid, e.g. helium, from the fluid reservoir 230. To this end, valves 208, 212, 214, 228 and 229 are in the opened state. All other valves are closed. As long as the stop valve 229 is opened, the system is filled with helium from the reservoir 230 such that the pressure tank 27, the pump 211, lines 210 and 215 as well as the vacuum tank 216 are being uniformly filled with helium.

Biasing:

After having terminated the filling procedure, stop valve 229 is closed and valve 212 is, furthermore, closed. Valve 208 remains in the state connecting the pressure tank 207 with line 210. In order to bias the system, the pump 211 is set in operation, pressing fluid from the vacuum tank 216 into the pressure tank 207. The process is carried out until a released fluid amount has reached the pressure tank 207 and a predetermined pressure difference has adjusted between the vacuum tank 216 and the pressure tank 207 or a predetermined pressure has been reached in the pressure tank 207, respectively. It may, for instance, be proceeded in a manner that a pressure of 3 bar is reached in the pressure tank 207, while the pressure in the vacuum tank 216 is reduced to 0.6 bar. After having completed the biasing of the system, all valves are closed.

Balloon Inflation:

To inflate the balloon 122, valve 224 is opened so that the pressure tank 207 is connected with the connection 203, and hence with the balloon 122, via line 209. Pressure equalization consequently occurs between the pressure tank 207 and the balloon 122, with valve 224 being maintained in the opened position until full pressure equalization between the pressure tank 207 and the balloon 122 has occurred. After full pressure equalization has been achieved, the balloon 122 and the pressure tank 207 are under the same pressure, for instance under a pressure of 1.2 bar.

Balloon Evacuation:

To evacuate the balloon, valve 222 is opened and valve 224 is closed, thereby disconnecting the pressure tank 207 from the connection 203. The balloon 122 is then directly connected with the vacuum tank 216 such that the evacuation of the balloon 122 is caused by pressure equalization between the balloon 122 and the vacuum tank 216. After full pressure equalization has been achieved, the balloon 122 and the vacuum tank 216 are under the same pressure, the pressure level being, for instance, 0.8 bar, yet in any case less than 1 bar.

The cycle of inflating and evacuating the balloon 122 can be repeated any number of times. For a renewed inflation of the balloon 122, the system may again be biased, to which end valve 222 is closed and valve 14 is opened. As before, valve 208 is in an open state in which the pressure tank 207 is connected with line 210 and valve 224 is closed. When the pump 211 is set in operation, fluid is sucked from the vacuum tank 216 and pressed into the pressure tank 207. To fill the balloon 122, valve 214 is again closed and valves 208 and 224 are switched such that the pressure tank 207 is connected with the connection 203, and hence with the balloon 122. After a pressure equalization of the pressure tank 207 and the balloon 122, the balloon is again filled. The evacuation of the balloon is again effected by switching valves 208 and 224 and opening valve 222 so as to connect the balloon 122 with the vacuum tank 216, thus causing fluid to flow from the balloon 122 into the vacuum tank 216 until pressure equalization between the balloon 122 and the vacuum tank 216 has occurred.

It should be apparent from the description herein that both the filling of the balloon 122 and the evacuation of the balloon 122 are simply effected due to a full pressure equalization with the pressure tank 207, on the one hand, and with the vacuum tank 216, on the other hand. The fluid is simply recirculated so as to enable a particularly economical mode of operation and a reduction of the energy consumption.

As a security measure valves 208 and 224 are blocked to each other in a hardware manner such that they cannot both be opened or both be closed at the same time.

As a further security measure the emergency valve 223 is opened if a pressure overload is detected based on the measurements of the pressure measurement devices 204, 205, 213, 225, 232, 233 and 234.

System Cleaning:

For cleaning purposes, valve 222 is opened and valve 208 is placed into a position in which the pressure tank 207 is connected with line 210. All other valves are closed. Condensate possibly collecting in the vacuum tank 216 can subsequently be pumped off by the vacuum-condensate pump 219.

The method of cyclically filling the balloon 122 can be realized in the form of a control algorithm which can be realized as a hardware circuit (electronic wiring with relays and flipflops) or software in a microcontroller. Typically, the realization is a software type realization, such as the software module as previously described.

The control algorithm can function as follows (when the computer software instructions are executed by the processor) to perform the following operations:

Determining the volume of the catheter with the balloon being in a deflated state based on at least two subsequent pressure measurements with two different pressures in the pressure tank 207. Thereby at least four measurement values (pressures at 204 and 205) are measured.

Measuring the pressures at 204 for a predetermined pressure at 232.

Stepwise raising the pressure in the pressure tank 207 until a predetermined or selected target value for the pressure at 204 is attained.

This is performed in the form of a control algorithm that is implemented as software instructions stored on a computer-readable memory device in the control system 140. In some embodiments, the control and inflation device 200 advantageously comprises a multi processor system, a pneumatic fluid circuit and an embedded PC for controlling an MMI for the application specific representation and evaluation of application and measurement data during one treatment. The multi processor system comprises at least two independent electronic circuits which monitor the security relevant function in a fail-safe manner.

According to some embodiments described herein, a method for determining a patient- and/or catheter-specifically optimized fluid amount for filling a balloon of a balloon catheter arranged in a body vessel to inflate the former is provided. The method may include the following steps:

a) evacuating the balloon, b) providing a defined starting amount of fluid and using this starting amount for filling the balloon as well as measuring the balloon starting pressure, c) providing a fluid amount increased relative to the preceding amount and using the increased amount for filling the balloon as well as measuring the balloon pressure, resulting from the filling or measuring variations thereof, d) comparing the measured balloon pressure or the variations thereof with a predetermined target value and repeating step c) until the balloon pressure or the variations thereof has reached said target value, e) storing the last-provided fluid amount as a reference value for inflating the balloon.

The aforementioned method can be used to determine a patient- and/or catheter-specifically optimized fluid amount for filling the balloon during the preparation of the occlusion procedure. Thus, prior to performing the patient's treatment, the optimum fluid amount for filling the balloon can be determined by the aforementioned method, with the optimum fluid amount determined being used as a reference value for the subsequent treatment of the patient, and the control and inflation device 200 for the balloon catheter 122 being adjusted to the patient- or catheter-specific value in this manner. During the subsequent occlusion cycles, the value determined using the aforementioned method is maintained or adjusted in order to take into account changes of the circumstances occurring during treatment. Adjusting the patient- and/or catheter-specifically determined value will be appropriate if, for example, the pressure conditions in the occluded vessel have changed, if the visco-elasticity of the vessel has changed, or if the treatment is shifted to another vessel site.

At the beginning of the method, the balloon 122 may be evacuated in order to bring the balloon 122 to a defined pressure level which serves as the starting point for the subsequent method steps. According to step b), a defined starting amount of fluid is provided and the starting amount is used for filling the balloon, whereupon the balloon pressure resulting from said starting amount is measured. According to step c), the preceding fluid amount can be increased and the balloon pressure resulting from the increased fluid amount is measured. The determined balloon pressure is compared with a predetermined target value, and the fluid amount used for filling the balloon may be gradually increased until the balloon pressure has reached the predetermined target value. A target value may, for instance, be an absolute value of at least 70 mm Hg, in particular approx. 80 mm Hg, independent of the patient concerned. The target value may, however, also be chosen as a function of the patient and, for instance, lie 10% above the maximum pressure resulting in the respective patient during the occlusion in the occluded vessel.

In order to achieve the predetermined target value, a differently strong inflation of the balloon (e.g., a differently large amount of introduced fluid) may be employed as a function of the visco-elasticity of the vessel, other patient-dependent factors and the catheter type. The gradual approach during the introduction of the fluid into the balloon 122 as in correspondence with the invention prevents the pressure in the balloon to exceed a predetermined target value. By defining as a reference value the fluid amount introduced into the balloon and corresponding to the target value, a pressure measurement in the balloon may (in some circumstances) be obviated during the subsequent inflation procedure, and the inflation procedure may be exclusively controlled on account of the introduced fluid amount. By limiting the introduced fluid amount, simple control of the inflation procedure is feasible while safeguarding against inadmissible operating states such as, in particular, inadmissible pressure states. If the reference value is be adjusted during subsequent inflating procedures, the balloon pressure may be continuously determined so that deviations of the balloon pressure from the target value can be detected, whereby the reference value is adjusted, if the detected deviation exceeds a predetermined limit of tolerance.

In some embodiments, a continuous pressure measurement is also useful, if the balloon pressure shall be monitored not only with regard to the holding of the target value but also with regard to exceeding a security relevant upper limit. Such an upper limit orients itself at values which are deemed as being permissive with regard to the operating security of the catheter, e.g. with respect to the bursting of the balloon or the coronary sinus vessel, and can have values of e.g. between 90 and 120 mm Hg. If the upper limit value is exceeded, the system can be stopped immediately.

According to an alternative embodiment, variations of the balloon pressure may be determined and analyzed instead of the absolute pressure prevailing in the balloon. Pressure variations can occur, if the balloon is inflated to an extent that the balloon touches the vessel wall, whereby the blood flow in the small gap between the balloon approaching the vessel wall and the vessel wall cause characteristic flow conditions that result in pressure variations in the balloon. Such pressure variations indicate that the balloon reaches the vessel wall.

According to some embodiments, the aforementioned steps b) to d) may comprise establishing a pressure-volume curve from the balloon starting volume resulting from using the starting amount and from the balloon starting pressure as well as the balloon volumes respectively resulting from using the gradually increased fluid amounts and from the respective balloon pressures. By way of the pressure-volume curve, it is feasible in a simple manner to observe and track the gradual approach to the optimum balloon filling, the course of the pressure-volume curve as a rule being such that in a first region, in which the balloon does not yet touch the vessel wall, the introduced fluid volume rises at a nearly constant or slightly increasing pressure and in a second region, in which the balloon abuts on the vessel wall, the internal pressure of the balloon significantly rises at every increase of the introduced fluid volume.

According to some embodiments, the balloon 122 may be evacuated prior to every performance or repetition of the aforementioned step c). Such an operation may ensure that a defined starting state is provided for each of the gradual increases in the fluid amount introduced into the balloon 122 in the course of the gradual approach to the target value of the balloon pressure, the balloon 122 after every evacuation being filled with a fluid amount increased relative to the preceding amount. In order to achieve the same evacuation state at every evacuation procedure, the balloon pressure may be measured during the evacuation of the balloon and said evacuation is effected until a predetermined negative pressure is reached. The predetermined negative pressure may be chosen to be the same at each evacuation. During the evacuation of the balloon 122, the pressure can additionally also be measured in the negative pressure source being responsible of the evacuation of the balloon. Advantageously, the pressure in the vacuum tank 216 can be measured in order to monitor if a predetermined negative pressure is attained.

The evacuation of the balloon 122 prior to each increase of the fluid amount introduced into the balloon 122 may also result in the balloon 122 being regularly deflated in the course of the method according to the invention, thus preventing too long an impairment or interruption of the flow in the concerned body vessel (e.g., the coronary sinus in some embodiments).

According to particular embodiments, it is provided that the increase in the fluid amount may be gradually effected by a value which is preferably the same at every increase.

According to some embodiments, the inflation of the balloon 122 is effected in that the starting amount of fluid and the respectively increased fluid amount are dosed into the pressure tank 207 and the balloon 122 is filled exclusively due to full pressure equalization between the pressure tank 207 and the balloon 122. The fluid is thus not directly filled into the balloon, since this would entail the risk of an uncontrolled amount of fluid entering the balloon in the event of a malfunction. If, as is preferably provided, the fluid is at first dosed into the pressure tank 207, the fluid amount can be precisely controlled and a malfunction would only result in the pressure tank 207 being filled with an excessive amount, which would, however, be detected or checked prior to the inflation of the balloon 122. With the respectively provided amount of fluid dosed into the pressure tank 207, filling of the balloon 122 is simply effected by opening the connection between the pressure tank 207 and the balloon 122, thus causing the balloon 122 to fill exclusively due to a full pressure equalization between the pressure tank 207 and the balloon 122.

According to an exemplary mode of operation, the pressure measured in the pressure tank 207 can be used for controlling the dosing of the desired amount of fluid into the pressure tank 207. With regard to the amount of fluid stored as a reference value, this means that the pressure that prevails due to the filling of the pressure tank 207 with the reference amount of fluid is stored as the reference pressure and the filling is carried out until the reference pressure is reached so that the control of the filling procedure of the pressure tank 207 is simplified.

According to a further mode of operation, it is provided that the balloon pressure is measured via a catheter lumen 206 separate from the catheter lumen 202 provided for filling. This will lead to an enhanced safety, in particular, if the balloon pressure is also measured in the catheter lumen provided for filling. In this manner, two independent pressure measurements are available, and possible malfunctions can be concluded from a comparison of these pressure values.

According to particular embodiments described herein, a method for inflating and evacuating the balloon 122 of the balloon catheter 120 is provided, in which the balloon 122 is connected with a positive pressure source for inflation and with a negative pressure source for evacuation and which is characterized in that the pressure tank 207 which is filled with fluid under positive pressure is provided as said positive pressure source, and that the inflation of the balloon 122 is effected exclusively due to a full pressure equalization between the pressure tank 207 and the balloon 122. By the inflation of the balloon 122 being effected exclusively due to a full pressure equalization between the pressure tank 207 and the balloon 122, malfunctions such as overfilling of the balloon 122 beyond the maximum pressure may be effectively avoided. The pressure tank 207 is initially filled with a predetermined fluid amount, said fluid amount being measured such that a predetermined filling state and pressure state will result in the balloon 122. When the connection between the prefilled pressure tank 207 and the balloon 122 is opened, a predetermined filling state of the balloon 122 will adjust due to the full pressure equalization between the pressure tank 207 and the balloon 122, thus causing the body vessel (e.g., the coronary sinus) to be occluded. By the filling of the balloon 122 being exclusively effected due to a full pressure equalization between the pressure tank 207 and the balloon 122, separate regulation and control measures can be obviated during filling, and an inadmissible filling state of the balloon may be prevented in that only the fluid amount initially dosed into the pressure tank 207 will reach the connection line and the balloon 122 because of the subsequent pressure equalization.

An additional control can be advantageously performed, if the inflation time is monitored. In case the inflation time lies below a lower limit value such as, e.g., 0.2 sec, an error message will be generated or the system shuts down. A too fast inflation might result in damage of the vessel. In case the inflation time lies above a predetermined upper limit value such as, e.g., 0.50 sec, an error message is also generated or the system shuts down. An inflation that lasts too long may result in that the blood flow in the respective vessel is impeded for a too long time.

A further control can advantageously be carried out when the deflation time is monitored. If the deflation time lies below a predetermined lower limit value such as, e.g., 0.5 sec, an error message is generated or the system shuts down. If the balloon collapses too fast, this might possibly lead to damage of the vessel.

In some embodiments, a cycle comprising the evacuation and inflation of the balloon may be advantageously performed by a sequence of the following steps:

a) connecting the balloon with a negative pressure source to evacuate the balloon, in particular to a predetermined negative pressure, b) interrupting the connection between the balloon and the negative pressure source, c) dosing a predetermined fluid amount into the pressure tank, thus filling the latter with fluid under positive pressure, d) opening the connection between the pressure tank and the balloon, whereby the inflation of the balloon is exclusively effected due to a full pressure equalization between the pressure tank and the balloon, e) closing the connection between the pressure tank and the balloon after full pressure equalization has occurred.

In an example mode of operation of this method, the vacuum tank 216 may be employed as said negative pressure source, the fluid preferably being recirculated between the vacuum tank 216, the pressure tank 207 and the balloon 122, thus offering the advantage that no new fluid need be fed into the loop even with a plurality of inflation and evacuation cycles. An advantageous mode of operation in this respect provides that the filling of the pressure tank 207 comprises the suction of fluid from the vacuum tank 216 forming the negative pressure source.

In some circumstances, it is further provided that the filling of the pressure tank 207 is effected by the aid of the pump 211 arranged between the pressure tank 207 and the vacuum tank 216.

The method can be advantageously carried out in that the fluid system comprising the pressure tank 207, the pump 211, the vacuum tank 216 and the balloon 122 as well as the connection lines is filled with such an amount of fluid that the pressure within the system is smaller than 2 bar at a full pressure equalization of all components. This will lead to a substantial enhancement of the operating safety, since it is ensured that an uncontrolled fluid amount will not enter the balloon 122 even if all of the safety valves or other safety devices have failed. In the most extreme case, pressure equalization would take place within the whole system at a valve failure, which, due to the overall quantity of the fluid present within the system, would result in a pressure of <2 bar so that an accordingly deflated state of the balloon 122 would be obtained.

According to a further aspect, the control and inflation device 200 of the control system 140 may comprise a connection for the inflation lumen 202 (refer also to the drive lumen 133 in FIG. 2) of the balloon catheter 120, wherein switching valves are arranged in a manner that the connection for the inflation lumen 202 is alternately connectable with the vacuum tank 216 and with the pressure tank 207. In a preferred manner, it is provided the pressure tank 207 is alternately connectable with the connection for the inflation lumen 202 and, via the pump 211, with the vacuum tank 216.

In some embodiments, the connection for a catheter lumen separate from the inflation lumen is provided, which is connected with a pressure measuring device.

In some embodiments, the pressure tank 207, the pump 211 and the vacuum tank 216 preferably form a closed fluid loop together with the inflation lumen 202 of the catheter. The closed loop preferably comprises a connection for filling the loop with fluid.

According to some embodiments, a control inflation apparatus for the balloon catheter 120 is provided comprising the pressure tank 207 for fluid, a dosing unit (e.g., the pump 211) for dosing fluid into the pressure tank 207, the connection 202 for a filling lumen of the balloon catheter 120, which connection can be connected to the pressure tank 207 via a switchable valve 24, at least one pressure measuring device for measuring the fluid pressure prevailing in the balloon 122 of the balloon catheter 120, and a control circuit to which the measuring values of the pressure measuring device are fed and which cooperates with the dosing unit for dosing a defined fluid amount into the pressure tank as a function of the pressure measurement values.

In one aspect, the control circuit cooperates with the switchable valve such that the switchable valve is closed if the dosing unit doses fluid into the pressure tank. The dosing unit can be comprised of a pump for example.

According to a further aspect, a pressure measuring device measuring the fluid pressure prevailing in the pressure tank can be provided, the measuring values of which are fed to the control circuit whereby a storage is provided for an upper pressure target value and the control circuit cooperates with the dosing unit such that dosing of fluid into the pressure tank is terminated if the pressure measured in the pressure tank reaches the pressure target value.

A number of embodiments of the invention have been described. Nevertheless, it will be understood that various modifications may be made without departing from the scope of the invention. Accordingly, other embodiments are within the scope of the following claims.

What is claimed is:

1. A method for determining a fluid amount for filling a balloon of a balloon catheter arranged in a body vessel, which comprises the steps of:

a) evacuating the balloon, b) after evacuating the balloon, providing a defined starting amount of gaseous fluid and using this starting amount for filling the balloon with the gaseous fluid as well as measuring the balloon starting pressure while the balloon is in the body vessel, c) providing a fluid amount of the gaseous fluid such that the total fluid amount of the gaseous fluid is increased relative to the preceding amount, and using the increased amount of the gaseous fluid for filling the balloon inside the body vessel as well as measuring the balloon pressure resulting from the filling or variations thereof, d) comparing the measured balloon pressure or variations thereof with a predetermined target value and repeating step c) until the measured balloon pressure or variations thereof has reached said predetermined target value, e) storing the last-provided fluid amount as a reference value for inflating the balloon during subsequent occlusion cycles in the body vessel, and f) inflating the balloon with the last-provided fluid amount of the gaseous fluid while the balloon is in the body vessel during subsequent occlusion cycles of the body vessel.

2. The method of claim 1, wherein steps b) to d) comprise establishing a pressure-volume curve from a balloon starting volume resulting from using the starting amount and from the balloon starting pressure as well as the balloon volumes respectively resulting from using the gradually increased fluid amounts and from the respective balloon pressures.

3. The method of claim 1, wherein the balloon is evacuated prior to every performance or repetition of step c).

4. The method of claim 3, wherein the balloon pressure is measured during the evacuation of the balloon and said evacuation is performed until a predetermined negative pressure is reached, said predetermined negative pressure being preferably chosen to be the same at each evacuation.

5. The method of claim 1, wherein the total fluid amount is increased relative to the preceding amount by an increment which is the same at each repetition of step c).

6. The method of claim 1, wherein the total fluid amount of the gaseous fluid is dosed into a pressure tank and the balloon is filled exclusively due to full pressure equalization between the pressure tank and the balloon.

7. The method of claim 6, wherein the pressure measured in the pressure tank is used for controlling the dosing of the total fluid amount into the pressure tank.

8. The method of claim 1, wherein the balloon pressure is measured via a catheter lumen separate from the catheter lumen provided for filling.

9. A method for inflating and evacuating the balloon of a balloon catheter, in which the balloon is connected with a positive pressure source for inflation and with a negative pressure source for evacuation, wherein a pressure tank which is filled with fluid under positive pressure is provided as said positive pressure source, the method comprising: inflating the balloon exclusively due to a full pressure equalization between the pressure tank and the balloon, and immediately evacuating the balloon in response to a detected pressure in the balloon reaching a value greater than an upper limit selected between 90 and 120 mm Hg.

10. The method of claim 9, wherein the balloon catheter is inserted in a coronary sinus for the pressure-controlled intermittent occlusion of the coronary sinus.

11. The method of claim 9, further comprising switching two or more valves to inflate the balloon and to subsequently evacuate the balloon, wherein the switching valves are arranged in a manner that a connection for an inflation lumen for the balloon is alternately connectable with the negative pressure source and with the pressure tank.

12. The method of claim 11, wherein the pressure tank is alternately connectable with the connection for the inflation lumen and, via a pump, with a vacuum tank of the negative pressure source.

13. The method of claim 9, further comprising detecting a pressure in a central catheter lumen that is separate from the inflation lumen, said central catheter lumen being connected with a pressure measuring device.

14. The method of claim 9, further comprising closing the connection between the pressure tank and the balloon after full pressure equalization has occurred.

* * * * *